(12) United States Patent
Park et al.

(10) Patent No.: US 11,629,123 B2
(45) Date of Patent: Apr. 18, 2023

(54) SELENOPSAMMAPLIN A AND DERIVATIVE THEREOF, PREPARATION METHOD THEREFOR, AND COMPOSITION FOR PREVENTING AND TREATING CANCER, CONTAINING SAME AS ACTIVE INGREDIENTS

(71) Applicant: SEOUL NATIONAL UNIVERSITY R & DB FOUNDATION, Seoul (KR)

(72) Inventors: Hyeung Geun Park, Seoul (KR); Sang Kook Lee, Seoul (KR); Hae Ju Han, Seoul (KR); Woong Sub Byun, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 256 days.

(21) Appl. No.: 16/762,685

(22) PCT Filed: Oct. 26, 2018

(86) PCT No.: PCT/KR2018/012826
§ 371 (c)(1),
(2) Date: May 8, 2020

(87) PCT Pub. No.: WO2019/093699
PCT Pub. Date: May 16, 2019

(65) Prior Publication Data
US 2021/0171458 A1  Jun. 10, 2021

(30) Foreign Application Priority Data

Nov. 9, 2017 (KR) .......................... 10-2017-0148790
Oct. 25, 2018 (KR) .......................... 10-2018-0128557

(51) Int. Cl.
*C07C 391/00* (2006.01)
*A61P 35/00* (2006.01)

(52) U.S. Cl.
CPC ............ *C07C 391/00* (2013.01); *A61P 35/00* (2018.01)

(58) Field of Classification Search
CPC .............................. C07C 391/00; A61P 35/00
See application file for complete search history.

(56) References Cited

U.S. PATENT DOCUMENTS

| 5,608,110 A | 3/1997 | Ramalingam et al. |
| 2009/0124667 A1 | 5/2009 | Ansorge et al. |

FOREIGN PATENT DOCUMENTS

| KR | 10-2014-0141904 A | 12/2014 |
| KR | 10-2016-0125989 A | 11/2016 |

OTHER PUBLICATIONS

Golub et al. Science, 1999, vol. 286, pp. 531-537.*
Kalal et al. Oncology Reviews, vol. 11, Mar. 2017, pp. 19-25.*
Yue et al., "Influence of reduction-sensitive diselenide bonds and disulfide bonds on oligoethylenimine conjugates for gene delivery", J. Mater. Chem. B., 2014, vol. 2, pp. 7210-7221.

* cited by examiner

*Primary Examiner* — Samira J Jean-Louis
(74) *Attorney, Agent, or Firm* — Vorys, Sater, Seymour and Pease LLP; Mih Suhn Koh

(57) ABSTRACT

The present invention relates to: novel selenopsammaplin A and a derivative thereof, which have anticancer activity; a preparation method therefor; and a pharmaceutical composition containing the same as active ingredients and, more specifically, to: a novel compound selenopsammaplin A and a derivative thereof which exhibit more excellent anticancer activity since a disulfide moiety thereof is substituted with diselenide according to research on the structural activity of psammaplin A, which is known to have an effect of inhibiting the growth of cancer cells; a preparation method therefor; and a composition for preventing or treating cancer, containing the same as active ingredients. According to the present invention, the novel selenopsammaplin A and the derivative thereof exhibit excellent anticancer activity on various human cancer cell lines so as to be expected to be effectively usable in a pharmaceutical composition for cancer prevention and treatment.

13 Claims, 4 Drawing Sheets

FIG. 3

| Compound code | X | Compound code | X |
|---|---|---|---|
| SSM-1 | 2-Br, 4-OH phenyl | SSM-15 | 2-Br, 4-OH phenyl |
| SSM-2 | 2-Cl, 4-OH phenyl | SSM-16 | 2-Cl, 4-OH phenyl |
| SSM-3 | 2-F, 4-OH phenyl | SSM-17 | 2-F, 4-OH phenyl |
| SSM-4 | phenyl | SSM-18 | phenyl |
| SSM-5 | 4-F phenyl | SSM-19 | 4-F phenyl |
| SSM-6 | 4-Cl phenyl | SSM-20 | 4-Cl phenyl |
| SSM-7 | 4-Br phenyl | SSM-21 | 4-Br phenyl |
| SSM-8 | 2,4-diF phenyl | SSM-22 | 2,4-diF phenyl |
| SSM-9 | 2,4-diCl phenyl | SSM-23 | 2,4-diCl phenyl |
| SSM-10 | 4-OEt phenyl | SSM-24 | 4-OEt phenyl |
| SSM-11 | 4-OBn phenyl | SSM-25 | 4-OBn phenyl |
| SSM-12 | 4-NO₂ phenyl | SSM-26 | 4-NO₂ phenyl |
| SSM-13 | 4-tBu phenyl | SSM-27 | 4-tBu phenyl |
| SSM-14 | naphthyl | SSM-28 | naphthyl |

SELENOPSAMMAPLIN A AND DERIVATIVE THEREOF, PREPARATION METHOD THEREFOR, AND COMPOSITION FOR PREVENTING AND TREATING CANCER, CONTAINING SAME AS ACTIVE INGREDIENTS

CROSS-REFERENCE TO RELATED APPLICATIONS

This application is a 371 of PCT/KR2018/012826, filed Oct. 26, 2018, which claims the benefit of priority from Korean Patent Application No. 10-2017-0148790, filed Nov. 9, 2017 and Korean Patent Application No. 10-2018-0128557, filed Oct. 25, 2018, the contents of each of which are incorporated herein by reference in its entirety.

TECHNICAL FIELD

The present invention relates to: novel selenopsammaplin A and a derivative thereof, which have anticancer activity; a preparation method therefor; a pharmaceutical composition containing the same as active ingredients; and the like.

BACKGROUND ART

Psammaplin A is a marine natural product and has a polymer structure in which monomers having a bromotyrosine structure are linked by a disulfide structure. The psammaplin A is known to have an antibacterial activity, the growth inhibition activity of a leukemia cell line P388, a DNA topoisomerase inhibitory activity, a histone deacetylase inhibitory activity, a DNA gyrase inhibitory activity, a farnesyltransferase inhibitory activity, a leucine aminopeptidase inhibitory activity, a PPAR-gamma activation activity, and the growth inhibition activity of colorectal cancer cells.

Recently, a research team led by Professor Jongheon Shin of the College of Pharmacy of Seoul National University has succeeded in isolating psammaplin A from sponge inhabiting the southern coast of the Korean Peninsula, revealed that the psammaplin A exhibits an inhibitory activity of cancer cells growth. Based on the findings, Hong et al. reported some compounds with a highly effective growth inhibition in lung cancer cells by performing structure-activity relationship studies of its derivatives (Hong S et al., (2017) Eur. J. Med. Chem. 96:218). In addition, the structure-activity relationship studies of psammaplin A derivatives for MRSA antibacterial activities were also conducted.

DISCLOSURE

Technical Problem

The present invention has been designed to solve the need in the related art as described above, and the present inventors confirmed an effect of preventing or treating cancer by preparing novel selenopsammaplin A and a derivative thereof, which have anticancer activity to inhibit the proliferation of cancer cells, thereby completing the present invention based on this.

Thus, an object of the present invention is to provide novel selenopsammaplin A and a derivative thereof, which have anticancer activity, and a pharmaceutically acceptable salt thereof.

Further, another object of the present invention is to provide a method for preparing novel selenopsammaplin A and a derivative thereof, which have anticancer activity.

In addition, another object of the present invention is to provide a pharmaceutical composition for preventing or treating cancer, containing novel selenopsammaplin A and a derivative thereof, which have anticancer activity, and a pharmaceutically acceptable salt thereof as active ingredients.

However, technical problems to be achieved by the present invention are not limited to the aforementioned problems, and other problems that are not mentioned may be clearly understood by those skilled in the art from the following description.

Technical Solution

To achieve the objects of the present invention as described above, the present invention provides selenopsammaplin A and a derivative thereof represented by the following Chemical Formula 1 or 2, an isomer thereof, or a pharmaceutically acceptable salt thereof.

[Chemical Formula 1]

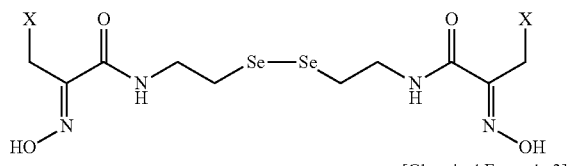

[Chemical Formula 2]

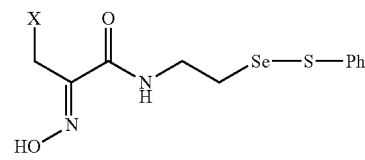

in Chemical Formulae 1 and 2,
X is hydrogen, a $C_{1-5}$ alkyl,

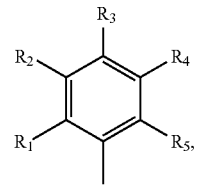

1-naphthyl, 2-naphthyl, or 9-anthracenyl;

in this case, $R_1$ to $R_5$ are each independently hydrogen, nitro, a halogen, cyan, hydroxy, dimethylamino, methylsulfonylamide, trifluoromethyl, a $C_{1-5}$ alkyl, a $C_{1-3}$ alkoxy, vinyl, aryl, phenoxy, or benzoxy;

when $R_3$ and $R_4$ are linked to a ring, the resulting structure is

(n = 1, 2, 3)

and when one of $R_1$ to $R_5$ is phenoxy or benzoxy, a substituent of the aromatic ring may be a $C_{1-3}$ alkyl, a $C_{1-3}$ alkoxy, a halogen, trifluoromethyl, or t-butyl.

As an exemplary embodiment of the present invention, X is

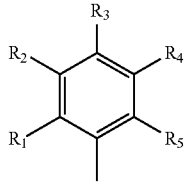

or 2-naphthyl;

in this case, $R_1$, $R_2$, and $R_5$ are each independently hydrogen;

$R_3$ is hydrogen, hydroxy, ethoxy, t-butyl, fluoro, chloro, bromo, nitro, or benzoxy; and $R_4$ may be hydrogen, bromo, chloro, or fluoro, but is not limited thereto.

Further, the present invention provides a method for preparing selenopsammaplin A and a derivative thereof represented by the following Chemical Formula 1, the method including: synthesizing a compound represented by the following Chemical Formula 4 by adding 2,2'-diselanediyldiethanamine to a compound represented by the following Chemical Formula 3; and synthesizing selenopsammaplin A and a derivative thereof represented by the following Chemical Formula 1 by subjecting the compound represented by Chemical Formula 4 to a hydrolysis reaction:

[Chemical Formula 3]

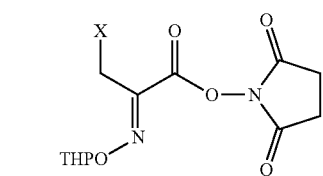

[Chemical Formula 4]

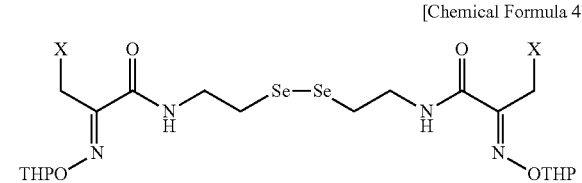

[Chemical Formula 1]

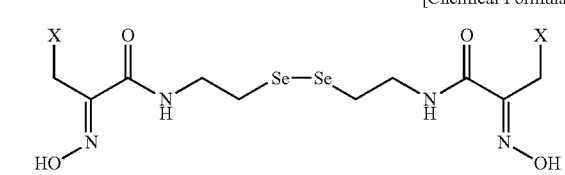

In addition, the present invention provides a method for preparing selenopsammaplin A and a derivative thereof represented by the following Chemical Formula 2, the method including: synthesizing selenopsammaplin A and a derivative thereof represented by the following Chemical Formula 2 by adding dithiothreitol to a compound represented by the following Chemical Formula 1:

[Chemical Formula 1]

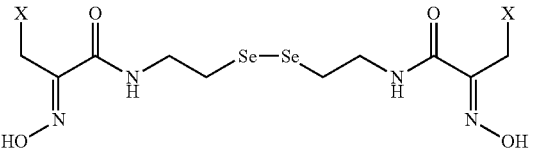

[Chemical Formula 2]

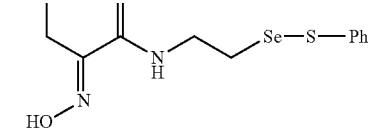

In Chemical Formula 2, Chemical Formula 3, and Chemical Formula 4, X is the same as that defined in Chemical Formula 1.

Furthermore, the present invention provides a pharmaceutical composition for preventing or treating cancer, containing the selenopsammaplin A and the derivative thereof represented by Chemical Formulae 1 and 2, an isomer thereof, or a pharmaceutically acceptable salt thereof as active ingredients.

As an exemplary embodiment of the present invention, the cancer may be lung cancer or colorectal cancer.

As another exemplary embodiment of the present invention, the selenopsammaplin A and the derivative thereof may be selected from the group consisting of the following compounds:

(2E,2'E)-N,N'-(diselanediylbis(ethane-2,1-diyl))bis(3-(3-bromo-4-hydroxyphenyl)-2-(hydroxyimino)propanamide); (2E,2'E)-N,N'-(diselanediylbis(ethane-2,1-diyl))bis(3-(3-chloro-4-hydroxyphenyl)-2-(hydroxyimino)propanamide); (2E,2'E)-N,N'-(diselanediylbis(ethane-2,1-diyl))bis(3-(3-fluoro-4-hydroxyphenyl)-2-(hydroxyimino)propanamide); (2E,2'E)-N,N'-(diselanediylbis(ethane-2,1-diyl))bis(2-(hydroxyimino)-3-phenyl propanamide); (2E,2'E)-N,N'-(diselanediylbis(ethane-2,1-diyl))bis(3-(4-fluorophenyl)-2-(hydroxyimino)propanamide); (2E,2'E)-N,N'-(diselanediylbis(ethane-2,1-diyl))bis(3-(4-chlorophenyl)-2-(hydroxyimino)propanamide); (2E,2'E)-N,N'-(diselanediylbis(ethane-2,1-diyl))bis(3-(4-bromophenyl)-2-(hydroxyimino)propanamide); (2E,2'E)-N,N'-(diselanediylbis(ethane-2,1-diyl))bis(3-(3,4-difluorophenyl)-2-(hydroxyimino)propanamide); (2E,2'E)-N,N'-(diselanediylbis(ethane-2,1-diyl))bis(3,4-dichlorophenyl)-2-(hydroxyimino)propanamide); (2E,2'E)-N,N'-(diselanediylbis(ethane-2,1-diyl))bis(3-(4-ethoxyphenyl)-2-(hydroxyimino)propanamide); (2E,2'E)-N,N'-(diselanediylbis(ethane-2,1-diyl))bis(3-(4-benzyloxy)phenyl)-2-(hydroxyimino)propanamide); (2E,2'E)-N,N'-(diselanediylbis(ethane-2,1-diyl))bis(2-(hydroxyimino)-3-(4-nitrophenyl)propanamide); (2E,2'E)-N,N'-(diselanediylbis(ethane-2,1-diyl))bis(3-(4-tert-butyl)phenyl)-2-(hydroxyimino)propanamide); (2E,2'E)-N,N'-(diselanediylbis(ethane-2,1-diyl))bis(2-(hydroxyimino)-3-(naphthalen-2-yl)propanamide); (E)-3-(3-bromo-4-hydroxyphenyl)-2-(hydroxyimino)-N-(2-((phenylthio)selanyl)ethyl)propanamide; (E)-3-(3-chloro-4-hydroxyphenyl)-2-(hydroxyimino)-N-(2-((phenylthio)selanyl)ethyl)propanamide; (E)-3-(3-fluoro-4-hydroxyphenyl)-2-(hydroxyimino)-N-(2-((phenylthio)selanyl)ethyl)propanamide; (E)-2-(hydroxyimino)-3-phenyl-N-(2-((phenylthio)selanyl)ethyl)propanamide; (E)-3-(4-fluorophenyl)-2-(hydroxyimino)-N-(2-((phenylthio)

selanyl)ethyl)propanamide; (E)-3-(4-chlorophenyl)-2-(hydroxyimino)-N-(2-((phenylthio)selanyl)ethyl) propanamide; (E)-3-(4-bromophenyl)-2-(hydroxyimino)-N-(2-((phenylthio)selanyl)ethyl)propanamide; (E)-3-(3,4-difluorophenyl)-2-(hydroxyimino)-N-(2-((phenylthio) selanyl)ethyl)propanamide; (E)-3-(3,4-dichlorophenyl)-2-(hydroxyimino)-N-(2-((phenylthio)selanyl)ethyl) propanamide; (E)-3-(4-ethoxyphenyl)-2-(hydroxyimino)-N-(2-((phenylthio)selanyl)ethyl)propanamide; (E)-3-(4-(benzyloxy)phenyl)-2-(hydroxyimino)-N-(2-((phenylthio) selanyl)ethyl)propanamide; (E)-2-(hydroxyimino)-3-(4-nitrophenyl)-N-(2-((phenylthio)selanyl)ethyl)propanamide; (E)-3-(4-(tert-butyl)phenyl)-2-(hydroxyimino)-N-(2-((phenylthio)selanyl)ethyl)propanamide; and (E)-2-(hydroxyimino)-3-(naphthalen-2-yl)-N-(2-((phenylthio)selanyl) ethyl)propanamide.

Furthermore, the present invention provides a method for preventing or treating cancer, the method including: administering the pharmaceutical composition to an individual.

In addition, the present invention provides a use of the pharmaceutical composition for preventing or treating cancer.

Advantageous Effects

The present invention provides a novel compound selenopsammaplin A and a derivative thereof in which a disulfide moiety thereof is substituted with a diselenide according to research on the structural activity of psammaplin A, which is known to have an effect of inhibiting the growth of cancer cells, and since it is confirmed that the psammaplin A and the derivative thereof exhibit excellent anticancer activity on various human cancer cells and exhibit a better effect of inhibiting the growth of cancer cells than existing psammaplin A, the novel compound is expected to be effectively usable in a pharmaceutical composition for cancer prevention and treatment.

DESCRIPTION OF DRAWINGS

FIG. 1 is a view illustrating the structures of novel selenopsammaplin A and a derivative thereof.

FIG. 3 is a view illustrating the chemical structures of selenopsammaplin A and derivative compounds thereof prepared by the method of the present invention.

MODES OF THE INVENTION

Figure 1A:
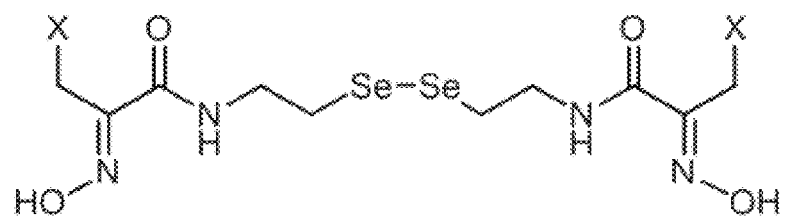
FIG. 1A is a view illustrating the structure of selenopsammaplin A and a derivative thereof of Chemical Formula 1.

The present invention provides novel selenopsammaplin A and a derivative thereof, which have anticancer activity, an isomer thereof, a pharmaceutically acceptable salt thereof, and a composition for preventing or treating cancer, containing the same as active ingredients. Further, since the compound according to the present invention exhibits an effect of preventing or treating cancer by inhibiting the growth of cancer cells, the compound may be usefully used for preventing or treating cancer.

Hereinafter, the present invention will be described in detail.

The present invention provides selenopsammaplin A and a derivative thereof represented by the following Chemical Formula 1 or 2, an isomer thereof, or a pharmaceutically acceptable salt thereof.

[Chemical Formula 1]

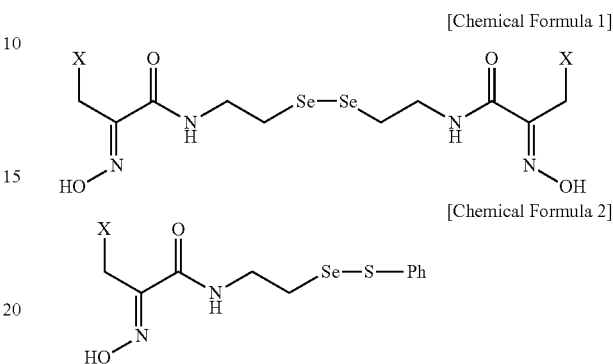

[Chemical Formula 2]

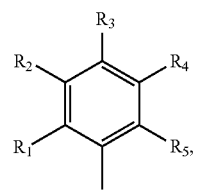

in the above Chemical Formulae 1 and 2,
X is hydrogen, a $C_{1-5}$ alkyl,

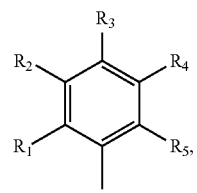

1-naphthyl, 2-naphthyl, or 9-anthracenyl;

in this case, $R_1$ to $R_5$ are each independently hydrogen, nitro, a halogen, cyan, hydroxy, dimethylamino, methylsulfonylamide, trifluoromethyl, a $C_{1-5}$ alkyl, a $C_{1-3}$ alkoxy, vinyl, aryl, phenoxy, or benzoxy;

when $R_3$ and $R_4$ are linked to a ring, the resulting structure is

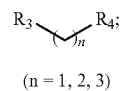

(n = 1, 2, 3)

and when one of $R_1$ to $R_5$ is phenoxy or benzoxy, a substituent of the aromatic ring may be a $C_{1-3}$ alkyl, a $C_{1-3}$ alkoxy, a halogen, trifluoromethyl, or t-butyl.

More preferably, X may be or 2-naphthyl; in this case, $R_1$, $R_2$, and $R_5$ may be each independently hydrogen; $R_3$ may be hydrogen, hydroxy, ethoxy, t-butyl, fluoro, chloro, bromo, nitro, or benzoxy; and $R_4$ may be hydrogen, bromo, chloro, or fluoro.

Hereinafter, the definitions of various substituents for preparing the compounds according to the present invention will be described.

As used herein, the term $C_{1-5}$ alkyl refers to a monovalent alkyl group having 1 to 5 carbon atoms, and the term $C_{1-3}$ alkyl refers to a monovalent alkyl group having 1 to 3 carbon atoms. Examples of the term include a functional group such as methyl, ethyl, n-propyl, i-propyl, n-butyl, i-butyl, tert-butyl, and n-hexyl.

Substituents including alkyls, and other alkyl moieties described in the present invention include both a straight-chained form and a branched form.

As used herein, the term $C_{1-3}$ alkoxy refers to a —O—R group, and here, R refers to "$C_1$-$C_3$ alkyl". Examples of a preferred alkoxy group include methoxy, ethoxy, phenoxy, and the like.

Substituents including alkyls, alkoxys, and other alkyl moieties described in the present invention include a straight-chained form and a branched form.

Preferred exemplary embodiments of selenopsammaplin A and a derivative thereof represented by Chemical Formula 1 or 2 according to the present invention are as follows:

((2E,2'E)-N,N'-(diselanediylbis(ethane-2,1-diyl))bis(3-(3-bromo-4-hydroxyphenyl)-2-(hydroxyimino)propanamide), SSM-1);

((2E,2'E)-N,N'-(diselanediylbis(ethane-2,1-diyl))bis(3-(3-chloro-4-hydroxyphenyl)-2-(hydroxyimino)propanamide), SSM-2);

((2E,2'E)-N,N'-(diselanediylbis(ethane-2,1-diyl))bis(3-(3-fluoro-4-hydroxyphenyl)-2-(hydroxyimino)propanamide), SSM-3);

((2E,2'E)-N,N'-(diselanediylbis(ethane-2,1-diyl))bis(2-(hydroxyimino)-3-phenylpropanamide), SSM-4);

((2E,2'E)-N,N'-(diselanediylbis(ethane-2,1-diyl))bis(3-(4-fluorophenyl)-2-(hydroxyimino)propanamide), SSM-5);

((2E,2'E)-N,N'-(diselanediylbis(ethane-2,1-diyl))bis(3-(4-chlorophenyl)-2-(hydroxyimino)propanamide), SSM-6);

((2E,2'E)-N,N'-(diselanediylbis(ethane-2,1-diyl))bis(3-(4-bromophenyl)-2-(hydroxyimino)propanamide), SSM-7);

((2E,2'E)-N,N'-(diselanediylbis(ethane-2,1-diyl))bis(3-(3,4-difluorophenyl)-2-(hydroxyimino)propanamide), SSM-8);

((2E,2'E)-N,N'-(diselanediylbis(ethane-2,1-diyl))bis(3-(3,4-dichlorophenyl)-2-(hydroxyimino)propanamide), SSM-9);

((2E,2'E)-N,N'-(diselanediylbis(ethane-2,1-diyl))bis(3-(4-ethoxyphenyl)-2-(hydroxyimino)propanamide), SSM-10);

((2E,2'E)-N,N'-(diselanediylbis(ethane-2,1-diyl))bis(3-(4-(benzyloxy)phenyl)-2-(hydroxyimino)propanamide), SSM-11);

((2E,2'E)-N,N'-(diselanediylbis(ethane-2,1-diyl))bis(2-(hydroxyimino)-3-(4-nitrophenyl)propanamide), SSM-12);

((2E,2'E)-N,N'-(diselanediylbis(ethane-2,1-diyl))bis(3-(4-tert-butyl)phenyl)-2-(hydroxyimino)propanamide), SSM-13);

((2E,2'E)-N,N'-(diselanediylbis(ethane-2,1-diyl))bis(2-(hydroxyimino)-3-(naphthalen-2-yl)propanamide), SSM-14);

((E)-3-(3-bromo-4-hydroxyphenyl)-2-(hydroxyimino)-N-(2-((phenylthio)selanyl)ethyl)propanamide, SSM-15);

((E)-3-(3-chloro-4-hydroxyphenyl)-2-(hydroxyimino)-N-(2-((phenylthio)selanyl)ethyl)propanamide, SSM-16);

((E)-3-(3-fluoro-4-hydroxyphenyl)-2-(hydroxyimino)-N-(2-((phenylthio)selanyl)ethyl)propanamide, SSM-17);

((E)-2-(hydroxyimino)-3-phenyl-N-(2-((phenylthio)selanyl)ethyl)propanamide, SSM-18);

((E)-3-(4-fluorophenyl)-2-(hydroxyimino)-N-(2-((phenylthio)selanyl)ethyl)propanamide, SSM-19);

((E)-3-(4-chlorophenyl)-2-(hydroxyimino)-N-(2-((phenylthio)selanyl)ethyl)propanamide, SSM-20);

((E)-3-(4-bromophenyl)-2-(hydroxyimino)-N-(2-((phenylthio)selanyl)ethyl)propanamide, SSM-21);

((E)-3-(3,4-difluorophenyl)-2-(hydroxyimino)-N-(2-((phenylthio)selanyl)ethyl)propanamide, SSM-22);

((E)-3-(3,4-dichlorophenyl)-2-(hydroxyimino)-N-(2-((phenylthio)selanyl)ethyl)propanamide, SSM-23);

((E)-3-(4-ethoxyphenyl)-2-(hydroxyimino)-N-(2-((phenylthio)selanyl)ethyl)propanamide, SSM-24);

((E)-3-(4-(benzyloxy)phenyl)-2-(hydroxyimino)-N-(2-((phenylthio)selanyl)ethyl)propanamide, SSM-25);

((E)-2-(hydroxyimino)-3-(4-nitrophenyl)-N-(2-((phenylthio)selanyl)ethyl)propanamide, SSM-26);

((E)-3-(4-(tert-butyl)phenyl)-2-(hydroxyimino)-N-(2-((phenylthio)selanyl)ethyl)propanamide, SSM-27); and ((E)-2-(hydroxyimino)-3-(naphthalen-2-yl)-N-(2-((phenylthio)selanyl)ethyl)propanamide, SSM-28).

The selenopsammaplin A and the derivative thereof represented by Chemical Formula 1 according to the present invention may be more preferably SSM-1, SSM-2, SSM-3, SSM-4, SSM-10, and SSM-12.

The compound of the present invention may be used in the form of a pharmaceutically acceptable salt, and as the salt, an acid addition salt formed by a pharmaceutically acceptable free acid is useful.

As the term salt used in the present invention, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylates, phenyl-substituted alkanoates, hydroxyalkanoates and alkanedioates, aromatic acids, aliphatic and aromatic sulfonic acids. Such pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, β-hydroxybutyrates, glycolates, malates, tartrates, methanesulfonates, propanesulfonates, naphthalene-1-sulfonates, naphthalene-2-sulfonates or mandelates.

The acid addition salt according to the present invention may be prepared by typical methods, for example, dissolving the compound in an excess aqueous acid solution, and precipitating this salt using a water-miscible organic solvent, for example, methanol, ethanol, acetone or acetonitrile. Further, the acid addition salt may also be prepared by evaporating the solvent or excess acid from this mixture, and then drying the mixture or suction-filtering a precipitated salt.

In addition, a pharmaceutically acceptable metal salt may be prepared using a base. An alkali metal or alkaline earth metal salt is obtained by, for example, dissolving the compound in an excess alkali metal hydroxide or alkaline earth metal hydroxide solution, filtering the non-soluble compound salt, evaporating the filtrate, and drying the result product. In this case, preparing a sodium, potassium or calcium salt as the metal salt is pharmaceutically suitable. A silver salt corresponding to this is obtained by reacting the alkali metal or alkaline earth metal salt with a suitable silver salt (for example, silver nitrate).

Further, the compound of the present invention includes not only pharmaceutically acceptable salts, but also all salts, isomers, hydrates and solvates which can be prepared by typical methods.

In addition, as another aspect of the present invention, the present invention may provide a method for preparing selenopsammaplin A and a derivative thereof represented by the following Chemical Formula 1, the method including: synthesizing a compound represented by the following Chemical Formula 4 by adding 2,2'-diselanediyldiethanamine to a compound represented by the following Chemical Formula 3; and synthesizing selenopsammaplin A and a derivative thereof represented by the following Chemical Formula 1 by subjecting the compound represented by Chemical Formula 4 to a hydrolysis reaction:

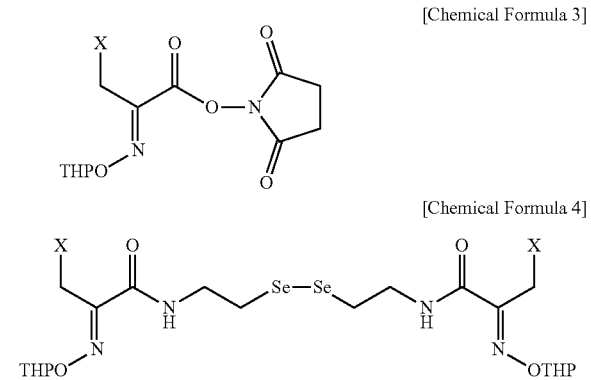

[Chemical Formula 3]

[Chemical Formula 4]

Furthermore, as still another aspect of the present invention, the present invention may provide a method for preparing selenopsammaplin A and a derivative thereof represented by the following Chemical Formula 2, the method including: synthesizing selenopsammaplin A and a derivative thereof represented by the following Chemical Formula 2 by adding dithiothreitol to a compound represented by the following Chemical Formula 1:

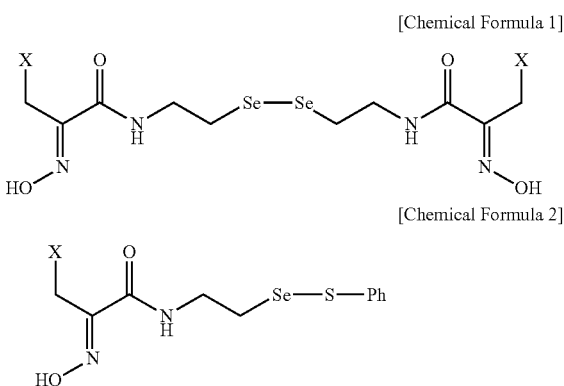

[Chemical Formula 1]

[Chemical Formula 2]

In Chemical Formula 2, Chemical Formula 3, and Chemical Formula 4, X is the same as that defined in Chemical Formula 1.

The compound of Chemical Formula 3 may be prepared by a method including the following steps, but is not limited to the following method:

synthesizing Compound 3 by a condensation reaction of Compound S with Compound 2 in a benzene solvent containing piperidine and an acetic acid catalyst;

synthesizing Compound 4 by adding tributyltinhydride (n-Bu$_3$SnH) to Compound 3 in a toluene solvent;

synthesizing Compound 5 by adding butyl nitrite (n-BuONO) to Compound 4 in the presence of an ethanolic ethoxide base;

synthesizing Compound 7 by obtaining Compound 6 by adding dihydropyran (DHP) to Compound 5 in the presence of a para-toluenesulfonic acid catalyst, and then performing a hydrolysis reaction; and synthesizing Compound 8 (Chemical Formula 3) by a condensation reaction of Compound 7 with N-hydroxysuccinimide.

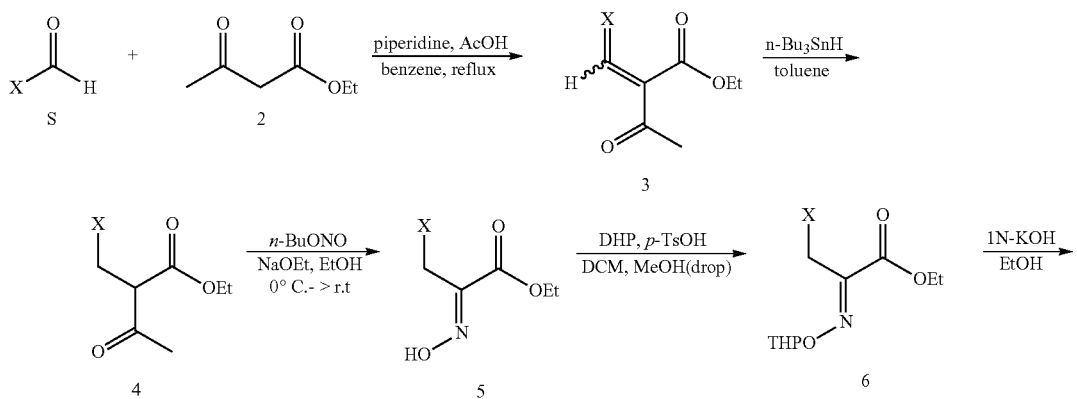

[Reaction Scheme 1]

-continued

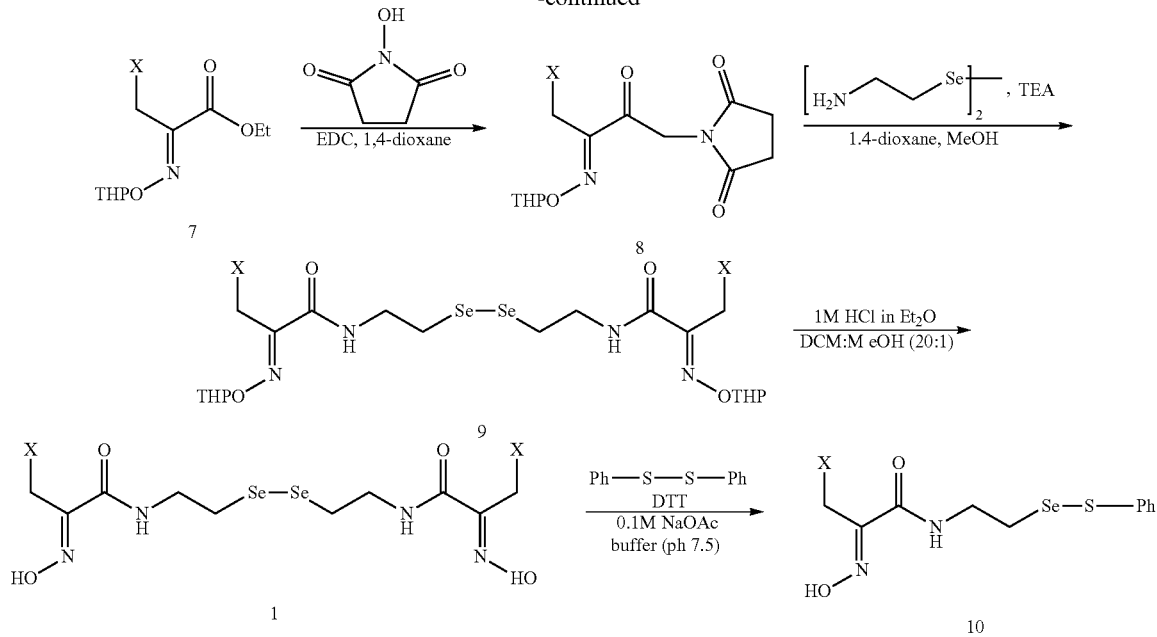

In Reaction Scheme 1, X is the same as that defined in Chemical Formula 1.

The method for preparing a compound belonging to the range of Chemical Formula 1 and Chemical Formula 2 is a method for preparing the compound by reactions according to Reaction Scheme 1, and α,β-unsaturated ethyl acetoacetate (Compound 3) is synthesized by a condensation reaction of a substrate (Compound S) in the form of a substituted arylaldehyde with ethyl acetoacetate (Compound 2) in a benzene solvent containing piperidine and an acetic acid catalyst (AcOH).

Then, ethyl acetoacetate (Compound 4) in which the alpha position is substituted is synthesized by allowing Compound 3 to react with tributyltinhydride (n-Bu₃SnH) in a toluene solvent. Then, an oxime (Compound 5) is synthesized by adding butyl nitrite (n-BuONO) to Compound 4 in the presence of an ethanolic ethoxide base. After Compound 6 was obtained by reacting Compound 5 with dihydropyran (DHP) in the presence of a p-toluenesulfonic acid (p-TsOH) catalyst, Compound 7 is synthesized by performing hydrolysis with an aqueous potassium hydroxide (1 N—KOH) solution in an ethanol solvent. Then, Compound 8 (a compound of Chemical Formula 3) is synthesized by a condensation reaction with N-hydroxysuccinimide and Compound 7 in a dioxane solvent (1,4-dioxane). Compound 9 (a compound of Chemical Formula 4) is produced by allowing 2,2'-diselanediyldiethanamine to react with synthesized Compound 8 (a compound of Chemical Formula 3) in the presence of a triethylamine (TEA) base, subsequently, a selenopsammaplin A derivative (Compound 1, a compound of Chemical Formula 1) is synthesized by performing a hydrolysis reaction using a hydrochloric acid (1 M-HCl) ether (Et₂O) solution as an acid catalyst, phenyl disulfide, dithiothreitol, and a phosphoric acid buffer are dissolved in a dimethyl sulfoxide solvent, and then a selenopsammaplin A derivative (Compound 10, a compound of Chemical Formula 2) is synthesized by diluting the reaction product thereof with ethyl acetate and separating the reaction product thereof with column chromatography.

In an exemplary embodiment of the present invention, after the selenopsammaplin A and the derivative thereof represented by Chemical Formula 1 or 2 were prepared, their structures were analyzed and confirmed by NMR or mass spectroscopy (see Examples 1 to 28). The forms of the substituents X of the compounds prepared according to Examples 1 to 28 are as shown in the following Table 1.

TABLE 1

| Compound code | X |
| --- | --- |
| SSM-1 | OH, Br (2-bromo-4-substituted phenol) |
| SSM-2 | OH, Cl (2-chloro-4-substituted phenol) |
| SSM-3 | OH, F (2-fluoro-4-substituted phenol) |

TABLE 1-continued
| Compound code | X |
|---|---|
| SSM-4 | 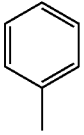 |
| SSM-5 | 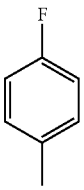 |
| SSM-6 | 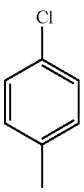 |
| SSM-7 | 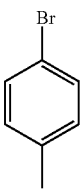 |
| SSM-8 | 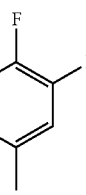 |
| SSM-9 | 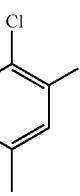 |
| SSM-10 | 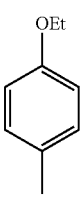 |
| SSM-11 | 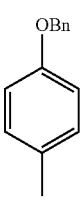 |
| SSM-12 | 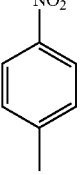 |
| SSM-13 | 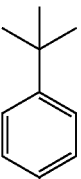 |
| SSM-14 | 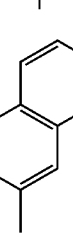 |
| SSM-15 | 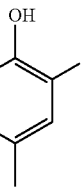 |
| SSM-16 | 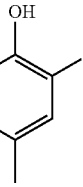 |
| SSM-17 | 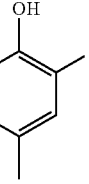 |
| SSM-18 |  |
| SSM-19 | 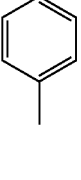 |

TABLE 1-continued

| Compound code | X |
|---|---|
| SSM-20 | 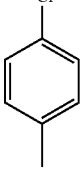 4-Cl-C6H4- |
| SSM-21 | 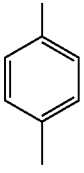 4-Br-C6H4- |
| SSM-22 | 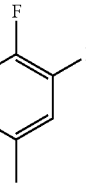 3,4-di-F-C6H3- |
| SSM-23 | 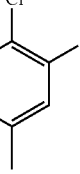 2,3-di-Cl-C6H3- |
| SSM-24 | 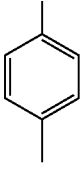 4-OEt-C6H4- |
| SSM-25 | 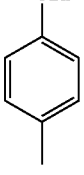 4-OBn-C6H4- |
| SSM-26 | 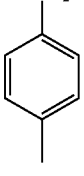 4-NO2-C6H4- |
| SSM-27 | 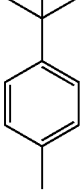 4-tBu-C6H4- |
| SSM-28 | 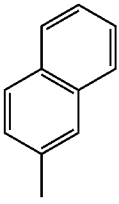 |

Furthermore, as another aspect of the present invention, the present invention provides a pharmaceutical composition for preventing, alleviating, or treating cancer, containing the selenopsammaplin A and the derivative thereof represented by Chemical Formulae 1 and 2, an isomer thereof, or a pharmaceutically acceptable salt thereof as active ingredients.

As used herein, the term prevention refers to all actions that suppress cancer or delay the onset of the cancer by administering the pharmaceutical composition according to the present invention.

As used herein, the term treatment refers to all actions that ameliorate or beneficially change symptoms caused by cancer by administering the pharmaceutical composition according to the present invention.

Cancer, which is a disease to be prevented or treated by the composition of the present invention, is classified as a disease in which normal tissue cells proliferate indefinitely for some reason and continue to grow rapidly regardless of the living phenomenon of the organism or the surrounding tissue condition, and the cancer in the present invention may be preferably lung cancer or colorectal cancer, but is not limited to these types.

In an exemplary embodiment of the present invention, anticancer activity on various human cancer cells was evaluated using selenopsammaplin A and a derivative thereof synthesized by the preparation method of the present invention (see Example 15), and it was confirmed that the compounds of the present invention SSM-1, SSM-2, SSM-3, SSM-4, SSM-10, and SSM-12 exhibited 20 to 60-fold more potent anticancer activity than a psammaplin A compound and exhibited excellent cancer cell growth inhibitory potential even compared to etoposide known to have anticancer activity in the related art.

Therefore, the selenopsammaplin A and the derivative thereof represented by Chemical Formulae 1 and 2 according to the present invention, an isomer thereof, or a pharmaceutically acceptable salt thereof may be usefully used as a pharmaceutical composition for preventing, alleviating, or treating cancer, containing the same as active ingredients.

The pharmaceutical composition according to the present invention may comprise a pharmaceutically acceptable carrier in addition to the active ingredient. In this case, the pharmaceutically acceptable carrier is typically used during formulation, and includes lactose, dextrose, sucrose, sorbitol, mannitol, starch, gum acacia, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, but is not limited thereto. Further, the pharmaceutically acceptable carrier may further include a lubricant, a wetting agent, a sweetening agent, a flavoring agent, an emulsifier, a preservative, and the like, in addition to the aforementioned ingredients.

The pharmaceutical composition of the present invention may be orally administered or may be parenterally administered (for example, applied intravenously, subcutaneously, intraperitoneally, or topically), and the administration dose may vary depending on a patient's condition and body weight, severity of disease, drug form, and administration route and period, but it may be properly selected by the person skilled in the art.

The pharmaceutical composition of the present invention is administered in a pharmaceutically effective amount. As used herein, the pharmaceutically effective amount refers to an amount sufficient to treat diseases at a reasonable benefit/risk ratio applicable to medical treatment, and an effective dosage level may be determined according to factors including the type of disease of patients, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by the person skilled in the art.

Specifically, an effective amount of the pharmaceutical composition of the present invention may vary depending on the age, sex, condition, and body weight of a patient, the absorption of the active ingredients in the body, inactivation rate and excretion rate, disease type, and the drugs used in combination, and in general, 0.001 to 150 mg, preferably 0.01 to 100 mg of the pharmaceutical composition of the present invention per 1 kg of a body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

As still another aspect of the present invention, the present invention provides a method for treating cancer, the method including administering the pharmaceutical composition to an individual. As used herein, the "individual" refers to a subject in need of treatment of a disease, and more specifically, refers to a mammal such as a human or a non-human primate, a mouse, a dog, a cat, a horse, and a cow.

As confirmed in Example 15 of the present invention, a novel compound selenopsammaplin A and a derivative thereof synthesized in the present invention exhibit excellent anticancer activity on human lung cancer and colorectal cancer cells so as to be expected to be effectively usable in a pharmaceutical composition for cancer prevention and treatment.

Hereinafter, preferred examples for helping the understanding of the present invention will be suggested. However, the following examples are provided only to more easily understand the present invention, and the contents of the present invention are not limited by the following examples.

Best Modes

Figure 2:
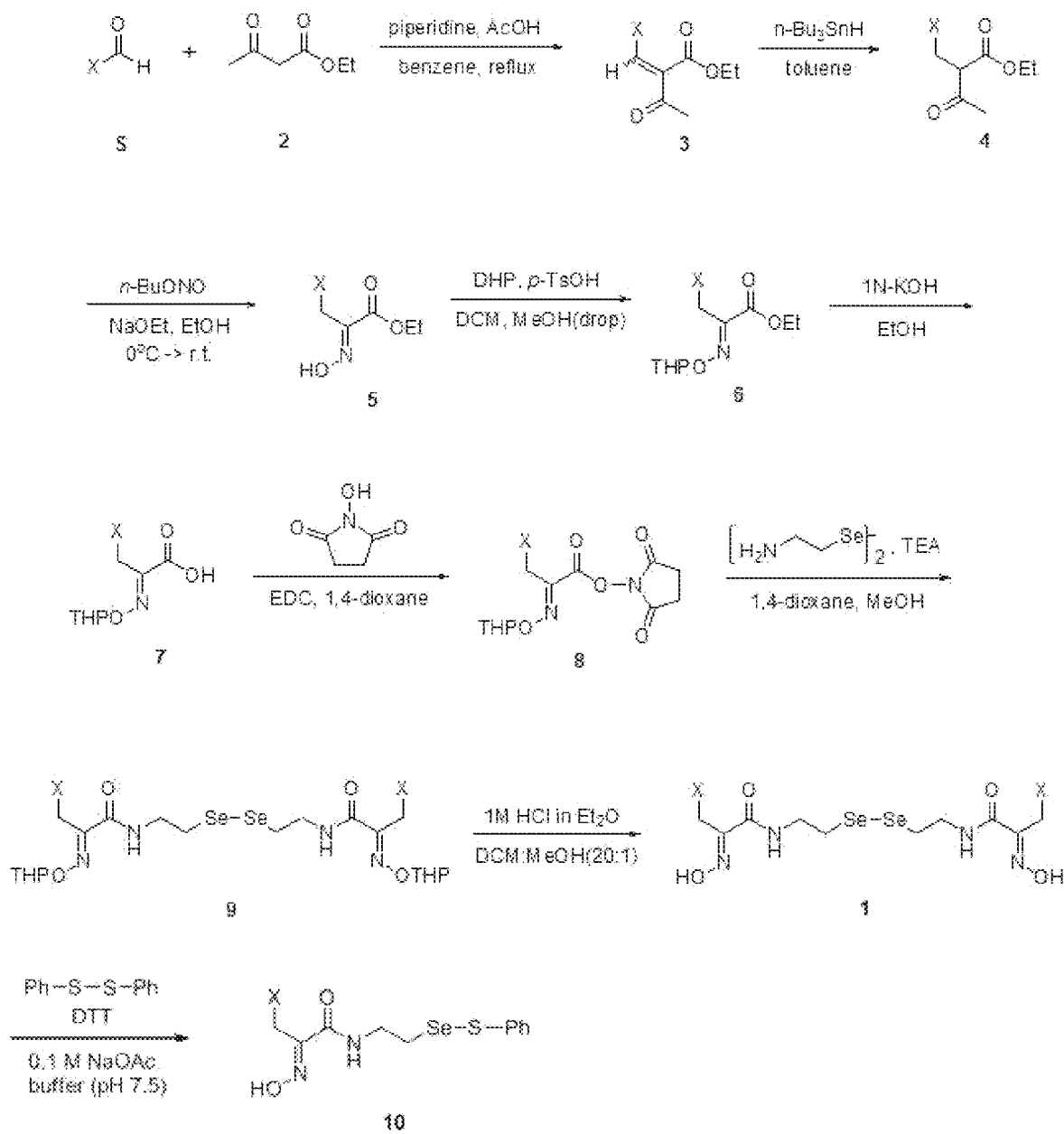
FIG. 2 is a view illustrating the process of preparing selenopsammaplin A and a derivative thereof.

In the present Examples 1 to 14, selenopsammaplin A and a derivative thereof as illustrated in FIG. 1A are prepared, and the compounds in Examples 1 to 14 are prepared according to the above-described Reaction Scheme 1 (FIG. 2). The synthesis examples of SSM-1 are shown below.

First, 2.587 g of α,β-unsaturated ethyl acetoacetate (Compound 3) was synthesized by a condensation reaction of 1.424 g of 3-bromo-4-hydroxybenzaldehyde (Compound S) with 2.0 g of ethyl acetoacetate (Compound 2) in 27.6 mL of a benzene solvent containing 108.1 μL of piperidine and 398.7 μL of an acetic acid catalyst (AcOH) for 3.5 hours. Then, 2.241 g of ethyl acetoacetate (Compound 4) in which the alpha position was substituted was synthesized by allowing 2.568 g of Compound 3 to react with 4.364 mL of tributyltinhydride (n-$Bu_3$SnH) in 40 mL of a toluene solvent for 1 hour. 1.482 g of an oxime (Compound 5) was synthesized by adding 911.3 μL of butyl nitrite (n-BuONO) to 42.233 g of the synthesized Compound 4 in 1.109 g of an ethanolic ethoxide base and 23 mL of an ethanol solvent to react for 18 hours. 1.372 g of Compound 6 was obtained by allowing 1.475 g of Compound 5 to react with 1.782 mL of dihydropyran (DHP) in 92.9 mg of a p-toluene sulfonic acid (p-TsOH) catalyst and 24 mL of a dichloromethane ($CH_2Cl_2$) solvent for 40 minutes. 1.167 g of Compound 7 was synthesized by hydrolyzing 1.363 g of synthesized Compound 6 with 10.6 mL of an aqueous potassium hydroxide (1 N—KOH) solution in an ethanol solvent for 3.5 hours. Then, 1.804 g of Compound 8 was synthesized by a condensation reaction of 1.618 g of Compound 7 with 987.6 mg of N-hydroxysuccinimide in 32 mL of a dioxane solvent (1,4-dioxane) using 1.472 g of 1-ethyl-3-(3-dimethylaminopropyl)carbodiimide for 21.5 hours. After 1.338 g of Compound 9 was synthesized by allowing 2,2'-diselanediyldiethanamine to react with 1.800 g of Compound 8 synthesized above in the presence of 1.103 mL of a triethylamine (TEA) base, 15 mL of a dioxane solvent (1,4-dioxane), and 15 mL of a methanol solvent for 2 hours, 897.8 mg of selenopsammaplin A (SSM-1) was synthesized by reacting 1.267 g of Compound 9 in 14.3 mL of a methanol solvent in the presence of a p-toluenesulfonic acid (p-TsOH) catalyst for 20 hours. Thereafter, compounds were also synthesized in Examples 2 to 14 in the same manner as described above.

Figure 1B:
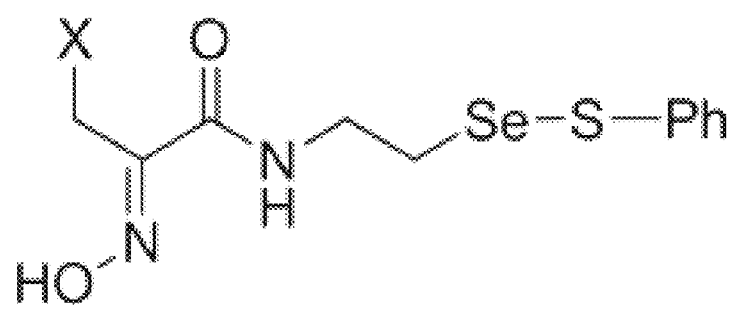
FIG. 1B is a view illustrating the structure of a selenopsammaplin A derivative of Chemical Formula 2.

Further, in the present Examples 1 to 28, a selenopsammaplin A monomer derivative as illustrated in FIG. 1B is prepared, and the compounds in Examples 1 to 28 are prepared according to the above-described Reaction Scheme 1 (FIG. 2). First, after synthesized selenopsammaplin A (1,133 mg) which is a substrate, phenyl disulfide (44.2 mg), and dithiothreitol (3.2 mg) were dissolved in a pH 8.3 phosphoric acid buffer (2 mL) and a dimethyl sulfoxide solvent (6 mL), the resulting solution was stirred at room temperature for 16 hours. After completion of the reaction, a selenopsammaplin A monomer (SSM-15, 35 mg) was obtained by separating the residue obtained by diluting the reaction solution with ethyl acetate (50 mL), washing the diluted reaction solution with water (10 mL×10), and distilling the resulting product under reduced pressure.

Nuclear magnetic resonance spectra (1H and 13C NMR) were recorded on a 800-MHz Bruker Avance III HD spectrometer with a 5-mm triple resonance inverse (TCI) Cryo-Probe spectrometer using DMSO-$d^6$, $CD_3OD$ and $CDCl_3$ solutions, and chemical transfer is described in units of parts per million (ppm). The resonance patterns are displayed along with s (singlet), d (doublet), t (triplet), q (quartet), quint (quintet), sext (sextet) and m (multiplet), and br is used to indicate a broad signal. The coupling constant (J) is expressed in Hertz (Hz).

Example 1. Preparation of (2E,2'E)-N,N'-(diselanediylbis(ethane-2,1-diyl))bis(3-(3-bromo-4-hydroxyphenyl)-2-(hydroxyimino)propanamide) (SSM-1)

According to the method of Reaction Scheme 1, SSM-1 was obtained using 3-bromo-4-hydroxybenzaldehyde as a starting material. (total yield: 23%).

$^1$H-NMR (800 MHz, DMSO-d$^6$): δ=11.84 (s, 2H), 10.02 (s, 2H), 8.10 (t, J=5.88 Hz, 2H), 7.29 (s, 2H), 7.01 (dd, J=8.28, 1.16 Hz, 2H), 6.83 (d, J=8.32 Hz, 2H), 3.45 (q, J=6.61 Hz, 4H), 3.01 (t, J=7.08 Hz, 4H) ppm

Example 2. Preparation of (2E,2'E)-N,N'-(diselanediylbis(ethane-2,1-diyl))bis(3-(3-chloro-4-hydroxyphenyl)-2-(hydroxyimino)propanamide) (SSM-2)

According to the method of Reaction Scheme 1, SSM-2 was obtained using 3-chloro-4-hydroxybenzaldehyde as a starting material. (total yield: 26%).

$^1$H-NMR (300 MHz, CD$_3$OD): δ=7.06 (dd, J$_1$=36.35 Hz, J$_2$=8.04 Hz, 8H), 3.85 (s, 4H), 3.47 (t, J=6.57 Hz, 4H), 2.76 (t, J=6.78 Hz, 4H), 2.23 (s, 6H) ppm

Example 3. Preparation of (2E,2'E)-N,N'-(diselanediylbis(ethane-2,1-diyl))bis(3-(3-fluoro-4-hydroxyphenyl)-2-(hydroxyimino)propanamide) (SSM-3)

According to the method of Reaction Scheme 1, SSM-3 was obtained using 3-fluoro-4-hydroxybenzaldehyde as a starting material. (total yield: 24%).

$^1$H-NMR (300 MHz, CD$_3$OD): δ=7.25-7.15 (m, 8H), 3.86 (s, 4H), 3.47 (t, J=6.6 Hz, 4H), 2.76 (t, J=6.96 Hz, 4H), 1.25 (s, 18H) ppm

Example 4. Preparation of (2E,2'E)-N,N'-(diselanediylbis(ethane-2,1-diyl))bis(2-(hydroxyimino)-3-phenylpropanamide) (SSM-4)

According to the method of Reaction Scheme 1, SSM-4 was obtained using benzaldehyde as a starting material. (total yield: 24%).

$^1$H-NMR (800 MHz, CD$_3$OD): δ=7.24 (d, J=7.68 Hz, 4H), 7.19 (t, J=7.68 Hz, 4H), 7.12 (t, J=7.36 Hz, 2H), 3.90 (s, 4H), 3.53 (t, J=6.92 Hz, 4H), 2.99 (t, J=6.92 Hz, 4H) ppm

Example 5. Preparation of (2E,2'E)-N,N'-(diselanediylbis(ethane-2,1-diyl))bis(3-(4-fluorophenyl)-2-(hydroxyimino)propanamide) (SSM-5)

According to the method of Reaction Scheme 1, SSM-5 was obtained using 4-fluorobenzaldehyde as a starting material. (total yield: 32%).

$^1$H-NMR (800 MHz, CD$_3$OD): δ=7.26 (m, 4H), 6.92 (t, J=8.8 Hz, 4H), 3.87 (s, 4H), 3.54 (t, J=6.96 Hz, 4H), 3.01 (t, J=6.96 Hz, 4H) ppm

Example 6. Preparation of (2E,2'E)-N,N'-(diselanediylbis(ethane-2,1-diyl))bis(3-(4-chlorophenyl)-2-(hydroxyimino)propanamide) (SSM-6)

According to the method of Reaction Scheme 1, SSM-6 was obtained using 4-chlorobenzaldehyde as a starting material. (total yield: 18%).

$^1$H-NMR (800 MHz, CD$_3$OD): δ=7.24 (m, 8H), 3.87 (s, 4H), 3.54 (t, J=6.96 Hz, 4H), 3.00 (t, J=6.96 Hz, 4H) ppm

Example 7. Preparation of (2E,2'E)-N,N'-(diselanediylbis(ethane-2,1-diyl))bis(3-(4-bromophenyl)-2-(hydroxyimino)propanamide) (SSM-7)

According to the method of Reaction Scheme 1, SSM-7 was obtained using 4-bromobenzaldehyde as a starting material. (total yield: 28%).

$^1$H-NMR (800 MHz, CD$_3$OD): δ=7.35 (d, J=10.8 Hz, 4H), 7.18 (d, J=8.48 Hz, 4H), 3.86 (s, 4H), 3.54 (t, J=6.96 Hz, 4H), 3.00 (t, J=6.92 Hz, 4H) ppm

Example 8. Preparation of (2E,2'E)-N,N'-(diselanediylbis(ethane-2,1-diyl))bis(3-(3,4-difluorophenyl)-2-(hydroxyimino)propanamide) (SSM-8)

According to the method of Reaction Scheme 1, SSM-8 was obtained using 3,5-difluorobenzaldehyde as a starting material. (total yield: 22%).

$^1$H-NMR (800 MHz, CD$_3$OD): δ=7.15 (m, 2H), 7.09 (m, 2H), 7.05 (m, 2H), 3.86 (d, J=5.36 Hz, 4H), 3.56 (t, J=6.92 Hz, 4H), 3.02 (t, J=6.96 Hz, 4H) ppm

Example 9. Preparation of (2E,2'E)-N,N'-(diselanediylbis(ethane-2,1-diyl))bis(3-(3,4-dichlorophenyl)-2-(hydroxyimino)propanamide) (SSM-9)

According to the method of Reaction Scheme 1, SSM-9 was obtained using 3,4-dichlorobenzaldehyde as a starting material. (total yield: 25%).

$^1$H-NMR (800 MHz, CD$_3$OD): δ=7.41 (d, J=2.00 Hz, 2H), 7.35 (d, J=8.24 Hz, 2H), 7.19 (dd, J=8.32, 2.00, 2H), 3.87 (s, 4H), 3.55 (t, J=6.92 Hz, 4H), 3.02 (t, J=6.92 Hz, 4H) ppm

Example 10. Preparation of (2E,2'E)-N,N'-(diselanediylbis(ethane-2,1-diyl))bis(3-(4-ethoxyphenyl)-2-(hydroxyimino)propanamide) (SSM-10)

According to the method of Reaction Scheme 1, SSM-10 was obtained using 4-ethoxybenzaldehyde as a starting material. (total yield: 27%).

$^1$H-NMR (800 MHz, CD$_3$OD): δ=11.77 (s, 2H), 8.06 (t, J=5.88 Hz, 2H), 7.10 (d, J=8.64 Hz, 4H), 6.78 (m, 4H), 3.95 (q, J=6.99 Hz, 4H), 3.72 (s, 4H), 3.44 (q, J=6.72 Hz, 4H), 3.00 (t, J=7.12 Hz, 4H), 1.28 (t, J=1.28 Hz, 6H) ppm

Example 11. Preparation of (2E,2'E)-N,N'-(diselanediylbis(ethane-2,1-diyl))bis(3-(4-(benzyloxy)phenyl)-2-(hydroxyimino)propanamide) (SSM-11)

According to the method of Reaction Scheme 1, SSM-11 was obtained using 4-benzyloxybenzaldehyde as a starting material. (total yield: 33%).

$^1$H-NMR (800 MHz, DMSO-d$^6$): δ=11.78 (s, 2H), 8.07 (t, J=5.88 Hz, 2H), 7.41 (d, J=7.20 Hz, 4H), 7.37 (t, J=7.60 Hz, 4H), 7.31 (t, J=7.32 Hz, 2H), 7.11 (d, J=8.64 Hz, 4H), 6.89 (d, J=11.36 Hz, 4H), 5.03 (s, 4H), 3.73 (s, 4H), 3.45 (q, J=6.69 Hz, 4H), 3.00 (t, J=7.12 Hz, 4H)

Example 12. Preparation of (2E,2'E)-N,N'-(diselanediylbis(ethane-2,1-diyl))bis(2-(hydroxyimino)-3-(4-nitrophenyl)propanamide) (SSM-12)

According to the method of Reaction Scheme 1, SSM-12 was obtained using 4-nitrobenzaldehyde as a starting material. (total yield: 29%).

¹H-NMR (800 MHz, CD₃OD): δ=8.09 (d, J=8.72 Hz, 4H), 7.49 (d, J=8.80 Hz, 4H), 4.02 (s, 4H), 3.55 (t, J=6.92 Hz, 4H), 3.02 (t, J=6.92 Hz, 4H) ppm Example 13. Preparation of (2E,2'E)-N,N'-(diselanediylbis(ethane-2,1-diyl))bis(3-(4-(tert-butyl)phenyl)-2-(hydroxyimino)propanamide) (SSM-13)

According to the method of Reaction Scheme 1, SSM-13 was obtained using 4-tert-butoxybenzaldehyde as a starting material. (total yield: 19%).
¹H-NMR (800 MHz, DMSO-d⁶): δ=11.79 (s, 2H), 8.07 (t, J=5.88 Hz, 2H), 7.25 (d, J=8.40H, 4H), 7.11 (d, J=8.16 Hz, 4H), 3.77 (s, 4H), 3.45 (q, J=6.69 Hz, 4H), 3.01 (t, J=7.12 Hz, 4H) ppm Example 14. Preparation of (2E,2'E)-N,N'-(diselanediylbis(ethane-2,1-diyl))bis(2-(hydroxyimino)-3-(naphthalen-2-yl)propanamide) (SSM-14)

According to the method of Reaction Scheme 1, SSM-14 was obtained using 4-2'-naphthylbenzaldehyde as a starting material. (total yield: 27%).
¹H-NMR (800 MHz, DMSO-d⁶): δ=11.93 (s, 1H), 8.15 (t, J=5.84 Hz, 1H), 7.82 (m, 2H), 7.80 (m, 4H), 7.67 (s, 2H), 7.45 (m, 4H), 7.40 (d, J=8.48 Hz, 2H), 3.98 (s, 4H), 3.46 (t, J=6.68H, 4H), 3.01 (t, J=7.08 Hz, 4H) ppm Example 15. Preparation of (E)-3-(3-bromo-4-hydroxyphenyl)-2-(hydroxyimino)-N-(2-((phenylthio)selanyl)ethyl)propanamide (SSM-15)

According to the method of Reaction Scheme X, SSM-15 was obtained using selenopsammaplin A (1) as a starting material. (total yield: 56%).
¹H-NMR (400 MHz, CD₃OD): δ 7.50-7.53 (m, 2H), 7.34 (d, J=1.8 Hz, 1H), 7.24 (dd, J=8.3, 6.9 Hz, 2H), 7.18 (d, J=7.4 Hz, 1H), 7.04 (dd, J=8.3, 2.3 Hz, 1H), 6.73 (d, J=8.3 Hz, 1H), 3.75 (s, 2H), 3.57 (t, J=6.9 Hz, 2H), 3.01 (t, J=6.9 Hz, 2H) ppm Example 16. Preparation of (E)-3-(3-chloro-4-hydroxyphenyl)-2-(hydroxyimino)-N-(2-((phenylthio)selanyl)ethyl)propanamide (SSM-16)

According to the method of Reaction Scheme X, SSM-16 was obtained using a selenopsammaplin A derivative (2) as a starting material. (total yield: 64%)
¹H-NMR (400 MHz, CD₃OD): δ 7.50-7.53 (m, 2H), 7.23 (d, J=2.3 Hz, 1H), 7.21 (dd, J=8.0, 6.6 Hz, 2H), 7.17 (t, J=7.3 Hz, 1H), 7.01 (dd, J=8.5, 2.1 Hz, 1H), 6.71 (d, J=8.2 Hz, 1H), 3.74 (s, 2H), 3.55 (t, J=7.1 Hz, 2H), 2.99 (t, J=6.9 Hz, 2H) ppm Example 17. Preparation of (E)-3-(3-fluoro-4-hydroxyphenyl)-2-(hydroxyimino)-N-(2-((phenylthio)selanyl)ethyl)propanamide (SSM-17)

According to the method of Reaction Scheme X, SSM-17 was obtained using a selenopsammaplin A derivative (3) as a starting material. (total yield: 62%)
¹H-NMR (400 MHz, CD₃OD): δ 7.50-7.53 (m, 2H), 7.23 (d, J=2.3 Hz, 1H), 7.21 (dd, J=8.0, 6.6 Hz, 2H), 7.02 (t, J=7.3 Hz, 1H), 6.91 (dd, J=8.5, 2.1 Hz, 1H), 6.70 (d, J=8.2 Hz, 1H), 3.74 (s, 2H), 3.55 (t, J=7.1 Hz, 2H), 2.98 (t, J=6.9 Hz, 2H) ppm Example 18. Preparation of (E)-2-(hydroxyimino)-3-phenyl-N-(2-((phenylthio)selanyl)ethyl)propanamide (SSM-18)

According to the method of Reaction Scheme X, SSM-18 was obtained using a selenopsammaplin A derivative (4) as a starting material. (total yield: 37%).
¹H-NMR (400 MHz, CD₃OD): δ 7.50-7.53 (m, 2H), 7.09-7.27 (m, 8H), 3.87 (d, J=5.1 Hz, 2H), 3.56 (t, J=6.9 Hz, 2H), 2.99 (t, J=6.9 Hz, 2H) ppm Example 19. Preparation of (E)-3-(4-fluorophenyl)-2-(hydroxyimino)-N-(2-((phenylthio)selanyl)ethyl)propanamide (SSM-19)

According to the method of Reaction Scheme X, SSM-19 was obtained using a selenopsammaplin A derivative (5) as a starting material. (total yield: 51%)
¹H-NMR (400 MHz, CD₃OD): δ 7.51-7.53 (m, 2H), 7.16-7.27 (m, 5H), 6.91 (t, J=9.0 Hz, 2H), 3.84 (s, 2H), 3.57 (t, J=6.9 Hz, 2H), 3.01 (t, J=7.1 Hz, 2H) ppm Example 20. Preparation of (E)-3-(4-chlorophenyl)-2-(hydroxyimino)-N-(2-((phenylthio)selanyl)ethyl)propanamide (SSM-20)

According to the method of Reaction Scheme X, SSM-20 was obtained using a selenopsammaplin A derivative (6) as a starting material. (total yield: 71%)
¹H-NMR (400 MHz, CD₃OD): δ 7.51-7.53 (m, 2H), 7.17-7.27 (m, 7H), 3.84 (s, 2H), 3.57 (t, J=6.9 Hz, 2H), 3.01 (t, J=6.9 Hz, 2H) ppm Example 21. Preparation of (E)-3-(4-bromophenyl)-2-(hydroxyimino)-N-(2-((phenylthio)selanyl)ethyl)propanamide (SSM-21)

According to the method of Reaction Scheme X, SSM-21 was obtained using a selenopsammaplin A derivative (7) as a starting material. (total yield: 34%)
¹H-NMR (400 MHz, CD₃OD): δ 7.52 (d, J=7.4 Hz, 2H), 7.15-7.35 (m, 7H), 3.83 (s, 2H), 3.57 (t, J=6.9 Hz, 2H), 3.01 (t, J=6.9 Hz, 2H) ppm Example 22. Preparation of (E)-3-(3,4-difluorophenyl)-2-(hydroxyimino)-N-(2-((phenylthio)selanyl)ethyl)propanamide (SSM-22)

According to the method of Reaction Scheme X, SSM-22 was obtained using a selenopsammaplin A derivative (8) as a starting material. (total yield: 35%)
¹H-NMR (400 MHz, CD₃OD): δ 7.51-7.53 (m, 2H), 7.04-7.27 (m, 6H), 3.84 (s, 2H), 3.58 (t, J=6.9 Hz, 2H), 3.02 (t, J=7.1 Hz, 2H) ppm Example 23. Preparation of (E)-3-(3,4-dichlorophenyl)-2-(hydroxyimino)-N-(2-((phenylthio)selanyl)ethyl)propanamide (SSM-23)

According to the method of Reaction Scheme X, SSM-23 was obtained using a selenopsammaplin A derivative (9) as a starting material. (total yield: 26%)
¹H-NMR (400 MHz, CD₃OD): δ 7.50-7.53 (m, 2H), 7.40 (d, J=2.3 Hz, 1H), 7.34 (d, J=8.2 Hz, 1H), 7.23-7.27 (m, 2H), 7.16-7.20 (m, 2H), 3.84 (s, 2H), 3.58 (t, J=6.9 Hz, 2H), 3.02 (t, J=6.9 Hz, 2H) ppm

Example 24. Preparation of (E)-3-(4-ethoxyphenyl)-2-(hydroxyimino)-N-(2-((phenylthio)selanyl)ethyl) propanamide (SSM-24)

According to the method of Reaction Scheme X, SSM-24 was obtained using a selenopsammaplin A derivative (10) as a starting material. (total yield: 40%)
$^1$H-NMR (400 MHz, CD$_3$OD): δ 7.51-7.53 (m, 2H), 7.12-7.27 (m, 5H), 6.73 (d, J=8.7 Hz, 2H), 3.94 (q, J=7.0 Hz, 2H), 3.79 (s, 2H), 3.56 (t, J=7.1 Hz, 2H), 2.99 (t, J=7.1 Hz, 2H), 1.32 (t, J=6.9 Hz, 3H) ppm

Example 25. Preparation of (E)-3-(4-(benzyloxy)phenyl)-2-(hydroxyimino)-N-(2-((phenylthio)selanyl)ethyl)propanamide (SSM-25)

According to the method of Reaction Scheme X, SSM-25 was obtained using a selenopsammaplin A derivative (11) as a starting material. (total yield: 41%)
$^1$H-NMR (400 MHz, CD$_3$OD): δ 7.52 (dt, J=7.0, 1.4 Hz, 2H), 7.14-7.39 (m, 9H), 6.82 (dd, J=6.7, 2.1 Hz, 2H), 4.98 (d, J=12.4 Hz, 2H), 3.80 (d, J=4.1 Hz, 2H), 3.55 (t, J=6.9 Hz, 2H), 2.99 (t, J=6.9 Hz, 2H) ppm

Example 26. Preparation of (E)-2-(hydroxyimino)-3-(4-nitrophenyl)-N-(2-((phenylthio)selanyl)ethyl)propanamide (SSM-26)

According to the method of Reaction Scheme X, SSM-26 was obtained using a selenopsammaplin A derivative (12) as a starting material. (total yield: 37%)
$^1$H-NMR (400 MHz, CD$_3$OD): δ 8.06-8.09 (m, 2H), 7.46-7.53 (m, 4H), 7.17-7.27 (m, 3H), 4.00 (d, J=2.8 Hz, 2H), 3.58 (t, J=6.9 Hz, 2H), 3.02 (t, J=6.9 Hz, 2H) ppm

Example 27. Preparation of (E)-3-(4-(tert-butyl)phenyl)-2-(hydroxyimino)-N-(2-((phenylthio)selanyl)ethyl)propanamide (SSM-27)

According to the method of Reaction Scheme X, SSM-27 was obtained using a selenopsammaplin A derivative (13) as a starting material. (total yield: 52%)
$^1$H-NMR (400 MHz, CD$_3$OD): δ 7.51-7.53 (m, 2H), 7.34 (d, J=2.3 Hz, 1H), 7.25 (t, J=7.5 Hz, 2H), 7.17 (t, J=7.3 Hz, 1H), 7.04 (dd, J=8.5, 2.1 Hz, 1H), 6.73 (d, J=8.2 Hz, 1H), 3.75 (s, 2H), 3.57 (t, J=7.1 Hz, 2H), 3.01 (t, J=6.9 Hz, 2H) ppm

Example 28. Preparation of (E)-2-(hydroxyimino)-3-(naphthalen-2-yl)-N-(2-((phenylthio)selanyl)ethyl) propanamide (SSM-28)

According to the method of Reaction Scheme X, SSM-28 was obtained using a selenopsammaplin A derivative (14) as a starting material. (total yield: 61%)
$^1$H-NMR (400 MHz, CD$_3$OD): δ 7.67-7.76 (m, 4H), 7.48-7.50 (m, 2H), 7.36-7.41 (m, 3H), 7.19-7.23 (m, 2H), 7.13-7.15 (m, 1H), 4.04 (s, 2H), 3.57 (t, J=6.9 Hz, 2H), 3.00 (t, J=6.9 Hz, 2H), 1.26 (s, 1H) ppm The forms of the substituents of the compounds prepared in Examples 1 to 28 are illustrated in FIG. 3.

Example 29. Determination of In Vitro Growth Inhibitory Efficacy of Selenopsammaplin a Derivative Compound Against Human Lung Cancer and Colorectal Cancer Cell Lines To confirm the in vitro growth inhibitory efficacy of the samples prepared in Examples 1 to 28 against human lung cancer and colorectal cancer cell lines, the experiments were performed as follows by applying the method described in the literature (Lee S K et al (2008) Chem Biol Interact 115:215-28). A human lung cancer cell line A549 and a colorectal cancer cell line HCT116 were acquired from the American Type Culture Collection (ATCC, Manassas, Va., USA) and used.

A549, HCT116 cells were subcultured once or twice weekly under conditions of 37° C. and 5% CO$_2$ using Roswell Park Memorial Institute (RPMI) Medium 1640 (RPMI 1640) containing 10% heat-inactivated Fetal Bovine Serum (FBS), 100 units/mL penicillin, 100 μg/mL streptomycin, and 250 ng/mL amphotericin B. All cells were thawed from liquid nitrogen, subcultured three times or more, and then used in the experiment.

The effects of the compounds obtained in Examples 1 to 28 on cell growth were measured by a sulforhodamine B (SRB) method (Lee et al (1998) Chem Biol Interact 115: 215-28).

Specifically, the human lung cancer and colon cancer cell lines used in the present invention were subcultured in a RPMI medium containing 10% FBS, 1% PSF, and the like, 10 μl of a sample dissolved in 10% DMSO and 190 μl (5×10$^4$ cells/ml) of the cell suspension were placed in each well of a 96-well plate. 190 μl of the cell suspension was placed in at least 16 wells, cultured for 30 minutes, and used as a negative control (zero-day control) before the experiment. The cultured cells were fixed with 10% trichloroacetic acid (TCA) and then stained with an SRB solution, the staining solution was dissolved with 10 mM Tris-base, and absorbance was measured at 515 nm. Using the cell culture in 10% DMSO as a control, cell viability according to the treatment with each test sample was measured using the following Equation 1.

% Cell viability=(OD(sample)−OD(0-day))/(OD(10% DMSO)−OD(0-day))×100     [Equation 1]

When the control in which the sample was not treated was defined as 100%, the value of the sample treatment group was shown as a percentage with respect to the control, and each test sample treatment was determined by the mean value±SEM of the duplicate or triplicate test. The IC$_{50}$ value is the concentration of the test sample for 50% viability. The effects of the compounds obtained in Examples 1 and 2 on lung cancer and colorectal cell lines are shown in the following Tables 2 and 3.

The experimental results are shown in Tables 2 and 3, and as can be confirmed in Tables 2 and 3, it was observed that among selenopsammaplin A derivative compounds, SSM-1, SSM-2, SSM-3, SSM-4, SSM-10, and SSM-12 showed 20 to 60-fold higher cancer cell growth inhibitory activity than psammaplin A itself, and particularly exhibited higher inhibitory activity than a control compound etoposide.

TABLE 2

| Compound | A549-LC$_{50}$ (μM) | HCT116-LC$_{50}$ (μM) |
|---|---|---|
| Etoposide | 0.42 | 0.90 |
| Psammaplin A | 1.76 | 0.61 |
| SSM-1 | 0.03 | 0.01 |
| SSM-2 | 0.05 | 0.02 |
| SSM-3 | 0.06 | 0.05 |
| SSM-4 | 0.08 | 0.09 |
| SSM-5 | 0.10 | 0.11 |
| SSM-6 | 0.25 | 0.28 |
| SSM-7 | 0.32 | 0.30 |
| SSM-8 | 0.20 | 0.19 |
| SSM-9 | 0.28 | 0.52 |

TABLE 2-continued

| Compound | A549-LC$_{50}$ (µM) | HCT116-LC$_{50}$ (µM) |
|---|---|---|
| SSM-10 | 0.05 | 0.07 |
| SSM-11 | 0.14 | 0.10 |
| SSM-12 | 0.09 | 0.09 |
| SSM-13 | 0.10 | 0.13 |
| SSM-14 | 0.38 | 0.12 |

TABLE 3

| Compound | A549-LC$_{50}$ (µM) | HCT116-LC$_{50}$ (µM) |
|---|---|---|
| Etoposide | 0.71 | 0.61 |
| Psammaplin A | 1.76 | 0.61 |
| SSM-15 | 0.10 | 0.01 |
| SSM-16 | 0.11 | 0.09 |
| SSM-17 | 0.29 | 0.20 |
| SSM-18 | 0.28 | 0.13 |
| SSM-19 | 0.49 | 0.33 |
| SSM-20 | 0.49 | 0.33 |
| SSM-21 | 0.51 | 0.18 |
| SSM-22 | 0.48 | 0.31 |
| SSM-23 | 0.28 | 0.05 |
| SSM-24 | 0.33 | 0.13 |
| SSM-25 | 0.18 | 0.08 |
| SSM-26 | 0.12 | 0.12 |
| SSM-27 | 0.11 | 0.02 |
| SSM-28 | 0.12 | 0.02 |

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

INDUSTRIAL APPLICABILITY

The present invention confirms that novel selenopsammaplin A and a derivative thereof have excellent anticancer activity on various human cancer cells and better growth inhibitory effect than existing psammaplin A, and the novel compound of the present invention is expected to be effectively usable in a pharmaceutical composition for cancer prevention and treatment.

The invention claimed is:

1. A compound of Chemical Formula 1 or 2, an isomer thereof, or a pharmaceutically acceptable salt thereof:

[Chemical Formula 1]

[Chemical Formula 2]

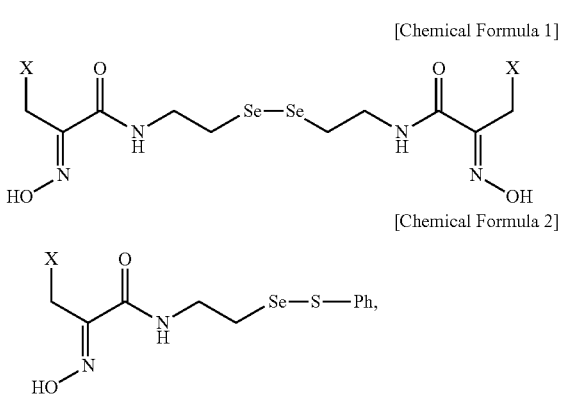

in Chemical Formulae 1 and 2,
X is hydrogen, a $C_{1-5}$ alkyl,

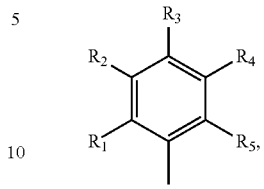

1-naphthyl, 2-naphthyl, or 9-anthracenyl, wherein $R_1$ to $R_5$ are each independently hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, or benzoxy; when $R_3$ and $R_4$ are linked to form a ring, the resulting structure is

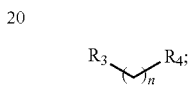

(n = 1, 2, 3)

and when one of $R_1$ to $R_5$ is phenoxy or benzoxy, the aromatic ring thereof may have a substituent of a $C_{1-3}$ alkyl, a $C_{1-3}$ alkoxy, a halogen, trifluoromethyl, or t-butyl.

2. The compound, the isomer thereof, or the pharmaceutically acceptable salt thereof of claim 1,
wherein X is

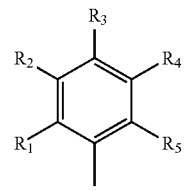

or 2-naphthyl, wherein $R_1$, $R_2$, and $R_5$ are each independently hydrogen;
$R_3$ is hydrogen, hydroxy, ethoxy, t-butyl, fluoro, chloro, bromo, nitro, or benzoxy; and
$R_4$ is hydrogen, bromo, chloro, or fluoro.

3. The compound, the isomer thereof, or the pharmaceutically acceptable salt thereof of claim 1, wherein The compound is any one selected from the group consisting of the following compounds:
(2E,2'E)-N,N'-(diselanediylbis(ethane-2,1-diyl))bis(3-(3-bromo-4-hydroxyphenyl)-2-(hydroxyimino)propanamide);
(2E,2'E)-N,N'-(diselanediylbis(ethane-2,1-diyl))bis(3-(3-chloro-4-hydroxyphenyl)-2-(hydroxyimino)propanamide);
(2E,2'E)-N,N'-(diselanediylbis(ethane-2,1-diyl))bis(3-(3-fluoro-4-hydroxyphenyl)-2-(hydroxyimino)propanamide);
(2E,2'E)-N,N'-(diselanediylbis(ethane-2,1-diyl))bis(2-(hydroxyimino)-3-phenylpropanamide);
(2E,2'E)-N,N'-(diselanediylbis(ethane-2,1-diyl))bis(3-(4-fluorophenyl)-2-(hydroxyimino)propanamide);
(2E,2'E)-N,N'-(diselanediylbis(ethane-2,1-diyl))bis(3-(4-chlorophenyl)-2-(hydroxyimino)propanamide);

(2E,2'E)-N,N'-(diselanediylbis(ethane-2,1-diyl))bis(3-(4-bromophenyl)-2-(hydroxyimino)propanamide);
(2E,2'E)-N,N'-(diselanediylbis(ethane-2,1-diyl))bis(3-(3,4-difluorophenyl)-2-(hydroxyimino)propanamide);
(2E,2'E)-N,N'-(diselanediylbis(ethane-2,1-diyl))bis(3,4-dichlorophenyl)-2-(hydroxyimino)propanamide);
(2E,2'E)-N,N'-(diselanediylbis(ethane-2,1-diyl))bis(3-(4-ethoxyphenyl)-2-(hydroxyimino)propanamide);
(2E,2'E)-N,N'-(diselanediylbis(ethane-2,1-diyl))bis(3-(4-benzyloxy)phenyl)-2-(hydroxyimino)propanamide);
(2E,2'E)-N,N'-(diselanediylbis(ethane-2,1-diyl))bis(2-(hydroxyimino)-3-(4-nitrophenyl)propanamide);
(2E,2'E)-N,N'-(diselanediylbis(ethane-2,1-diyl))bis(3-(4-tert-butyl)phenyl)-2-(hydroxyimino)propanamide);
(2E,2'E)-N,N'-(diselanediylbis(ethane-2,1-diyl))bis(2-(hydroxyimino)-3-(naphthalen-2-yl)propanamide);
(E)-3-(3-bromo-4-hydroxyphenyl)-2-(hydroxyimino)-N-(2-((phenylthio)selanyl)ethyl)propanamide;
(E)-3-(3-chloro-4-hydroxyphenyl)-2-(hydroxyimino)-N-(2-((phenylthio)selanyl)ethyl)propanamide;
(E)-3-(3-fluoro-4-hydroxyphenyl)-2-(hydroxyimino)-N-(2-((phenylthio)selanyl)ethyl)propanamide;
(E)-2-(hydroxyimino)-3-phenyl-N-(2-((phenylthio)selanyl)ethyl)propanamide;
(E)-3-(4-fluorophenyl)-2-(hydroxyimino)-N-(2-((phenylthio)selanyl)ethyl)propanamide;
(E)-3-(4-chlorophenyl)-2-(hydroxyimino)-N-(2-((phenylthio)selanyl)ethyl)propanamide;
(E)-3-(4-bromophenyl)-2-(hydroxyimino)-N-(2-((phenylthio)selanyl)ethyl)propanamide;
(E)-3-(3,4-difluorophenyl)-2-(hydroxyimino)-N-(2-((phenylthio)selanyl)ethyl)propanamide;
(E)-3-(3,4-dichlorophenyl)-2-(hydroxyimino)-N-(2-((phenylthio)selanyl)ethyl)propanamide;
(E)-3-(4-ethoxyphenyl)-2-(hydroxyimino)-N-(2-((phenylthio)selanyl)ethyl)propanamide;
(E)-3-(4-(benzyloxy)phenyl)-2-(hydroxyimino)-N-(2-((phenylthio)selanyl)ethyl)propanamide;
(E)-2-(hydroxyimino)-3-(4-nitrophenyl)-N-(2-((phenylthio)selanyl)ethyl)propanamide;
(E)-3-(4-(tert-butyl)phenyl)-2-(hydroxyimino)-N-(2-((phenylthio)selanyl)ethyl)propanamide; and
(E)-2-(hydroxyimino)-3-(naphthalen-2-yl)-N-(2-((phenylthio)selanyl)ethyl)propanamide.

4. The compound, the isomer thereof, or the pharmaceutically acceptable salt thereof of claim 3, wherein the compound is any one selected from the group consisting of the following compounds:
(2E,2'E)-N,N'-(diselanediylbis(ethane-2,1-diyl))bis(3-(3-bromo-4-hydroxyphenyl)-2-(hydroxyimino)propanamide);
(2E,2'E)-N,N'-(diselanediylbis(ethane-2,1-diyl))bis(3-(3-chloro-4-hydroxyphenyl)-2-(hydroxyimino)propanamide);
(2E,2'E)-N,N'-(diselanediylbis(ethane-2,1-diyl))bis(3-(3-fluoro-4-hydroxyphenyl)-2-(hydroxyimino)propanamide);
(2E,2'E)-N,N'-(diselanediylbis(ethane-2,1-diyl))bis(2-(hydroxyimino)-3-phenylpropanamide);
(2E,2'E)-N,N'-(diselanediylbis(ethane-2,1-diyl))bis(3-(4-ethoxyphenyl)-2-(hydroxyimino)propanamide); and
(2E,2'E)-N,N'-(diselanediylbis(ethane-2,1-diyl))bis(2-(hydroxyimino)-3-(4-nitrophenyl)propanamide).

5. A method for preparing a compound of represented by the following Chemical Formula 1, the method comprising:
synthesizing a compound represented by the following Chemical Formula 4 by adding 2,2'-diselanediyldiethanamine to a compound represented by the following Chemical Formula 3; and
synthesizing the compound of represented by the following Chemical Formula 1 by subjecting the compound represented by Chemical Formula 4 to a hydrolysis reaction:

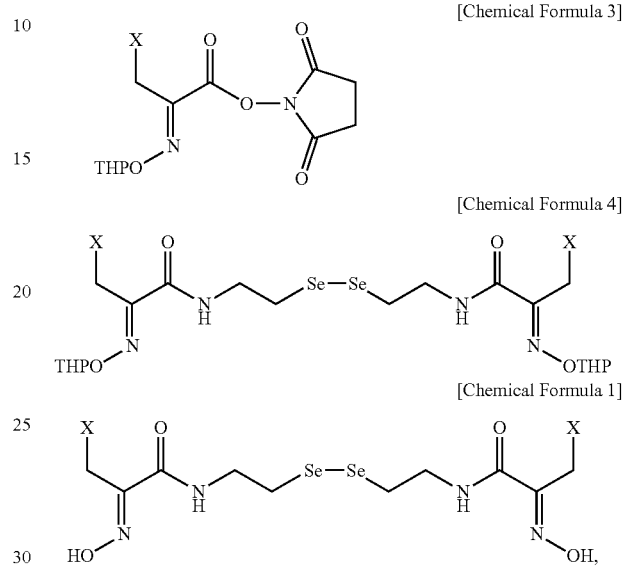

in Chemical Formula 1, Chemical Formula 3, and Chemical Formula 4,

X is hydrogen, a $C_{1-5}$ alkyl,

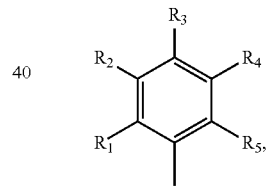

1-naphthyl, 2-naphthyl, or 9-anthracenyl, wherein $R_1$ to $R_5$ are each independently hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, or benzoxy; when $R_3$ and $R_4$ are linked to form a ring, the resulting structure is

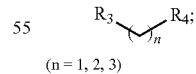

(n = 1, 2, 3)

and when one of $R_1$ to $R_5$ is phenoxy or benzoxy, a substituent of the aromatic ring thereof is a $C_{1-3}$ alkyl, a $C_{1-3}$ alkoxy, a halogen, trifluoromethyl, or t-butyl.

6. A method for preparing a compound represented by the following Chemical Formula 2, the method comprising:
synthesizing the compound represented by the following Chemical Formula 2 by adding dithiothreitol to a compound represented by the following Chemical Formula 1:

[Chemical Formula 1]

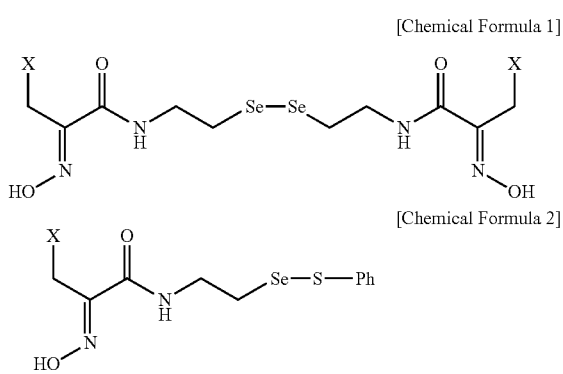

[Chemical Formula 2]

in Chemical Formulae 1 and 2,
X is hydrogen, a $C_{1-5}$ alkyl,

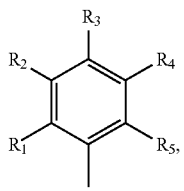

1-naphthyl, 2-naphthyl, or 9-anthracenyl,
wherein $R_1$ to $R_5$ are each independently hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, or benzoxy;
when $R_3$ and $R_4$ are linked to form a ring, the resulting structure is

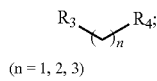

(n = 1, 2, 3)

and
when one of $R_1$ to $R_5$ is phenoxy or benzoxy, a substituent of the aromatic ring thereof is a $C_{1-3}$ alkyl, a $C_{1-3}$ alkoxy, a halogen, trifluoromethyl, or t-butyl.

7. The method of claim 5, wherein X is

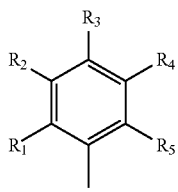

or 2-naphthyl;
$R_1$, $R_2$, and $R_5$ are each independently hydrogen;
$R_3$ is hydrogen, hydroxy, ethoxy, t-butyl, fluoro, chloro, bromo, nitro, or benzoxy; and
$R_4$ is hydrogen, bromo, chloro, or fluoro.

8. A pharmaceutical composition for treating lung cancer or colorectal cancer, comprising the compound, an isomer thereof, or a pharmaceutically acceptable salt thereof of claim 1 as active ingredients.

9. A method for treating lung cancer or colorectal cancer, the method comprising: administering a compound represented by the following Chemical Formula 1 or 2, an isomer thereof, or a pharmaceutically acceptable salt thereof as an active ingredient to a subject in need thereof:

[Chemical Formula 1]

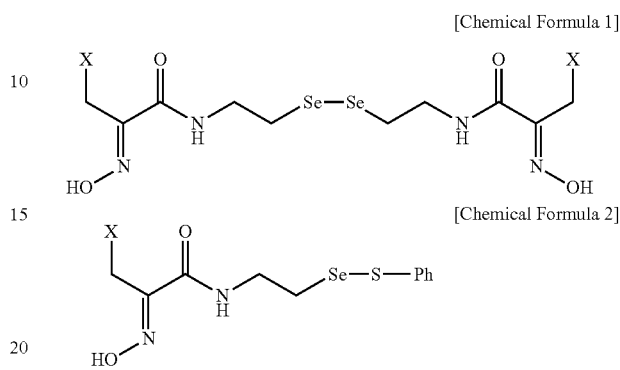

[Chemical Formula 2]

in Chemical Formulae 1 and 2,
X is hydrogen, a $C_{1-5}$ alkyl,

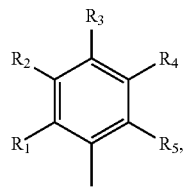

1-naphthyl, 2-naphthyl, or 9-anthracenyl, wherein
$R_1$ to $R_5$ are each independently hydrogen, nitro, a halogen, cyano, hydroxy, dimethylamino, methylsulfonylamide, trifluoromethyl, a $C_{1-5}$ alkyl, a $C_{1-3}$ alkoxy, vinyl, aryl, phenoxy, or benzoxy; when $R_3$ and $R_4$ are linked to form a ring, the resulting structure is

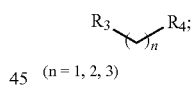

(n = 1, 2, 3)

and when one of $R_1$ to $R_5$ is phenoxy or benzoxy, a substituent of the aromatic ring thereof is a $C_{1-3}$ alkyl, a $C_{1-3}$ alkoxy, a halogen, trifluoromethyl, or t-butyl.

10. The method of claim 9,
wherein X is

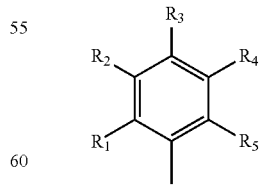

or 2-naphthyl,
wherein $R_1$, $R_2$, and $R_5$ are each independently hydrogen,
$R_3$ is hydrogen, hydroxy, ethoxy, t-butyl, fluoro, chloro, bromo, nitro, or benzoxy, and $R_4$ is hydrogen, bromo, chloro, or fluoro.

11. The method of claim 9, wherein the compound is any one selected from the group consisting of the following compounds:

- (2E,2'E)-N,N'-(diselanediylbis(ethane-2,1-diyl))bis(3-(3-bromo-4-hydroxyphenyl)-2-(hydroxyimino)propanamide);
- (2E,2'E)-N,N'-(diselanediylbis(ethane-2,1-diyl))bis(3-(3-chloro-4-hydroxyphenyl)-2-(hydroxyimino)propanamide);
- (2E,2'E)-N,N'-(diselanediylbis(ethane-2,1-diyl))bis(3-(3-fluoro-4-hydroxyphenyl)-2-(hydroxyimino)propanamide);
- (2E,2'E)-N,N'-(diselanediylbis(ethane-2,1-diyl))bis(2-(hydroxyimino)-3-phenylpropanamide);
- (2E,2'E)-N,N'-(diselanediylbis(ethane-2,1-diyl))bis(3-(4-fluorophenyl)-2-(hydroxyimino)propanamide);
- (2E,2'E)-N,N'-(diselanediylbis(ethane-2,1-diyl))bis(3-(4-chlorophenyl)-2-(hydroxyimino)propanamide);
- (2E,2'E)-N,N'-(diselanediylbis(ethane-2,1-diyl))bis(3-(4-bromophenyl)-2-(hydroxyimino)propanamide);
- (2E,2'E)-N,N'-(diselanediylbis(ethane-2,1-diyl))bis(3-(3,4-difluorophenyl)-2-(hydroxyimino)propanamide);
- (2E,2'E)-N,N'-(diselanediylbis(ethane-2,1-diyl))bis(3,4-dichlorophenyl)-2-(hydroxyimino)propanamide);
- (2E,2'E)-N,N'-(diselanediylbis(ethane-2,1-diyl))bis(3-(4-ethoxyphenyl)-2-(hydroxyimino)propanamide);
- (2E,2'E)-N,N'-(diselanediylbis(ethane-2,1-diyl))bis(3-(4-benzyloxy)phenyl)-2-(hydroxyimino)propanamide);
- (2E,2'E)-N,N'-(diselanediylbis(ethane-2,1-diyl))bis(2-(hydroxyimino)-3-(4-nitrophenyl)propanamide);
- (2E,2'E)-N,N'-(diselanediylbis(ethane-2,1-diyl))bis(3-(4-tert-butyl)phenyl)-2-(hydroxyimino)propanamide);
- (2E,2'E)-N,N'-(diselanediylbis(ethane-2,1-diyl))bis(2-(hydroxyimino)-3-(naphthalen-2-yl)propanamide);
- (E)-3-(3-bromo-4-hydroxyphenyl)-2-(hydroxyimino)-N-(2-((phenylthio)selanyl)ethyl)propanamide;
- (E)-3-(3-chloro-4-hydroxyphenyl)-2-(hydroxyimino)-N-(2-((phenylthio)selanyl)ethyl)propanamide;
- (E)-3-(3-fluoro-4-hydroxyphenyl)-2-(hydroxyimino)-N-(2-((phenylthio)selanyl)ethyl)propanamide;
- (E)-2-(hydroxyimino)-3-phenyl-N-(2-((phenylthio)selanyl)ethyl)propanamide;
- (E)-3-(4-fluorophenyl)-2-(hydroxyimino)-N-(2-((phenylthio)selanyl)ethyl)propanamide;
- (E)-3-(4-chlorophenyl)-2-(hydroxyimino)-N-(2-((phenylthio)selanyl)ethyl)propanamide;
- (E)-3-(4-bromophenyl)-2-(hydroxyimino)-N-(2-((phenylthio)selanyl)ethyl)propanamide;
- (E)-3-(3,4-difluorophenyl)-2-(hydroxyimino)-N-(2-((phenylthio)selanyl)ethyl)propanamide;
- (E)-3-(3,4-dichlorophenyl)-2-(hydroxyimino)-N-(2-((phenylthio)selanyl)ethyl)propanamide;
- (E)-3-(4-ethoxyphenyl)-2-(hydroxyimino)-N-(2-((phenylthio)selanyl)ethyl)propanamide;
- (E)-3-(4-(benzyloxy)phenyl)-2-(hydroxyimino)-N-(2-((phenylthio)selanyl)ethyl)propanamide;
- (E)-2-(hydroxyimino)-3-(4-nitrophenyl)-N-(2-((phenylthio)selanyl)ethyl)propanamide;
- (E)-3-(4-(tert-butyl)phenyl)-2-(hydroxyimino)-N-(2-((phenylthio)selanyl)ethyl)propanamide; and
- (E)-2-(hydroxyimino)-3-(naphthalen-2-yl)-N-(2-((phenylthio)selanyl)ethyl)propanamide.

12. The method of claim 11, wherein the compound is any one selected from the group consisting of the following compounds:

- (2E,2'E)-N,N'-(diselanediylbis(ethane-2,1-diyl))bis(3-(3-bromo-4-hydroxyphenyl)-2-(hydroxyimino)propanamide);
- (2E,2'E)-N,N'-(diselanediylbis(ethane-2,1-diyl))bis(3-(3-chloro-4-hydroxyphenyl)-2-(hydroxyimino)propanamide);
- (2E,2'E)-N,N'-(diselanediylbis(ethane-2,1-diyl))bis(3-(3-fluoro-4-hydroxyphenyl)-2-(hydroxyimino)propanamide);
- (2E,2'E)-N,N'-(diselanediylbis(ethane-2,1-diyl))bis(2-(hydroxyimino)-3-phenylpropanamide);
- (2E,2'E)-N,N'-(diselanediylbis(ethane-2,1-diyl))bis(3-(4-ethoxyphenyl)-2-(hydroxyimino)propanamide); and
- (2E,2'E)-N,N'-(diselanediylbis(ethane-2,1-diyl))bis(2-(hydroxyimino)-3-(4-nitrophenyl)propanamide).

13. The method of claim 6, wherein X is

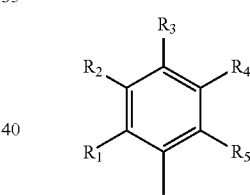

or 2-naphthyl,
wherein $R_1$, $R_2$, and $R_5$ are each independently hydrogen; $R_3$ is hydrogen, hydroxy, ethoxy, t-butyl, fluoro, chloro, bromo, nitro, or benzoxy; and $R_4$ is hydrogen, bromo, chloro, or fluoro.

* * * * *